United States Patent
Holash et al.

(10) Patent No.: US 7,351,411 B2
(45) Date of Patent: Apr. 1, 2008

(54) METHODS OF TREATING ANEMIA BY INHIBITION OF VASCULAR ENDOTHELIAL GROWTH FACTOR (VEGF)

(75) Inventors: Jocelyn Holash, Alameda, CA (US); Jesse M. Cedarbaum, Larchmont, NY (US); John Rudge, Mahopac, NY (US); George D. Yancopoulos, Yorktown Heights, NY (US); Neil Stahl, Carmel, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 159 days.

(21) Appl. No.: 11/373,358

(22) Filed: Mar. 10, 2006

(65) Prior Publication Data

US 2006/0210566 A1    Sep. 21, 2006

Related U.S. Application Data (60) Provisional application No. 60/660,638, filed on Mar. 11, 2005.

(51) Int. Cl.
*A61K 38/18*  (2006.01)
*C07K 14/71*  (2006.01)
*C12N 15/62*  (2006.01)

(52) U.S. Cl. .................. 424/134.1; 424/192.1; 514/2; 514/12; 530/350; 536/23.4

(58) Field of Classification Search ............ None
See application file for complete search history.

(56) References Cited

U.S. PATENT DOCUMENTS

| 6,897,294 B2 * | 5/2005 | Davis-Smyth et al. ...... 530/350 |
| 2003/0175276 A1 | 9/2003 | Thorpe et al. |
| 2004/0115166 A1 | 6/2004 | Hayward et al. |

FOREIGN PATENT DOCUMENTS

WO    WO 2005/016369    2/2005

OTHER PUBLICATIONS

Tam, B. Y., et al. (2004) Blood 104(11): 595.
Richard, S., et al. (2002) Blood 99(10):3851-3853.

* cited by examiner

*Primary Examiner*—Christine J Saoud
*Assistant Examiner*—Jon M Lockard
(74) *Attorney, Agent, or Firm*—Valeta Gregg, Esq.

(57) ABSTRACT

Methods of treating anemic disorders in human subjects comprising administering a VEGF antagonist comprising a fusion polypeptide having an immunoglobulin-like (Ig) domain 2 of the VEGF receptor Flt1 and Ig domain 3 of the VEGF receptor Flk1 or Flt4, and a multimerizing component. Further included are methods of preventing anemia, increasing hematocrit levels, and increasing or stimulating erythropoietin, particularly in subjects being treated for cancer with chemotherapeutic agents and/or radiation.

12 Claims, 3 Drawing Sheets

METHODS OF TREATING ANEMIA BY INHIBITION OF VASCULAR ENDOTHELIAL GROWTH FACTOR (VEGF)

CROSS-REFERENCE TO RELATED APPLICATIONS

This application claims the benefit under 35 USC § 119(e) of U.S. Provisional 60/660,638 filed 11 Mar. 2005, which application is herein specifically incorporated by reference in its entirety.

BACKGROUND

1. Field of the Invention

The field of the invention is generally related to methods of treating anemia with an agent capable of blocking, inhibiting, or ameliorating vascular endothelial growth factor (VEGF).

2. Description of Related Art

The production of red blood cells in mammals, erythropoiesis, is under the control of the hormone erythropoietin (EPO). EPO is normally present in low concentrations in plasma, where it is sufficient to maintain equilibrium between normal blood cell loss (i.e., through aging) and red blood cell production.

Anemia is a decrease in red blood cell mass caused by decreased production or increased destruction of red blood cells. EPO is currently used for treatment of the anemias associated with end-stage renal failure, acquired immunodeficiency syndrome (AIDS), and anemia associated with cancer chemotherapy. See for example, U.S. Pat. No. 5,846,528. Other groups of anemic disorders, resulting from an inherited abnormality in globin production, are hemoglobinopathies, including thalassemias, results from inherited defects in the rate of synthesis of one or more of the globin chains.

US 2004/0115166 describes the treatment of autoimmune hemolytic anemia with a inhibitor of VEGF-B. US 2003/0175276 describes a method of inhibiting angiogenesis with an anti-VEGF antibody for the treatment of sickle cell anemia.

BRIEF SUMMARY OF THE INVENTION

In a first aspect, the invention features a method of treating an anemic disorder comprising administering to a human subject a vascular endothelial growth factor (VEGF) antagonist capable of blocking, inhibiting, or ameliorating VEGF-mediated activity. More specifically, the VEGF antagonist a high affinity fusion protein dimer (or "trap") comprising a fusion polypeptide having an immunoglobulin-like (Ig) domain 2 of the VEGF receptor Flt1 and Ig domain 3 of the VEGF receptor Flk1 or Flt4, and a multimerizing component. Even more specifically, the VEGF antagonist comprises a fusion polypeptide selected from the group consisting of acetylated Flt-1(1-3)-Fc, Flt-1(1-3$_{R->N}$)-Fc, Flt-1(1-3$_{AB}$)-Fc, Flt-1(2-3$_{AB}$)-Fc, Flt-1(2-3)-Fc, Flt-1D2-VEGFR3D3-FcΔC1(a), Flt-1D2-Flk-1D3-FcΔC1(a), and VEGFR1R2-FcΔC1(a). In a preferred embodiment, the VEGF antagonist is one of Flt1D2.Flk1D3.FCΔC1(a) (SEQ ID NO:2) or, more preferably, VEGFR1R2-FcΔC1 (a) (SEQ ID NO:4).

The anemic disorder treated by the method of the invention is selected from the group consisting of anemia associated with chronic renal failure, cancer, cancer chemotherapy and antiviral therapy. The anemic disorder may also be nutritional iron-deficiency (hypoferric) anemia, blood-loss (hemorrhagic) anemia, or hemolytic anemia. Preferably, the subject treated by the methods of the invention has been or will be treated with chemotherapy or radiation.

Administration of the agent may be by any method known in the art, including subcutaneous, intramuscular, intradermal, intraperitoneal, intravenous, intranasal, or oral routes of administration. Administration may be by single or multiple doses.

In a second aspect, the invention features a method of preventing anemia resulting from or expected to result from cancer chemotherapy in a subject at risk, comprising administering to a human subject a vascular endothelial growth factor (VEGF) antagonist capable of blocking, inhibiting, or ameliorating VEGF-mediated activity, wherein the VEGF antagonist is a fusion polypeptide consisting of an immunoglobulin-like (Ig) domain 2 of the VEGF receptor Flt1 and Ig domain 3 of the VEGF receptor Flk1 or Flt4, and a multimerizing component. In a preferred embodiment, the VEGF antagonist is one of Flt1D2.Flk1D3.FcΔC1(a) (SEQ ID NO:2) or VEGFR1R2-FcΔC1(a) (SEQ ID NO:4). In a preferred embodiment, the subject treated is a subject undergoing or who will undergo treatment with radiation and/or chemotherapy.

In a third aspect, the invention features a method of increasing hematocrit level in a subject in need thereof, comprising administering to a human subject a vascular endothelial growth factor (VEGF) antagonist comprising a fusion polypeptide having an immunoglobulin-like (Ig) domain 2 of the VEGF receptor Flt1 and Ig domain 3 of the VEGF receptor Flk1 or Flt4, and a multimerizing component. In a preferred embodiment, the VEGF antagonist is one of Flt1D2.Flk1D3.FcΔC1(a) (SEQ ID NO:2) or VEGFR1R2-FcΔC1(a) (SEQ ID NO:4). In one embodiment, the subject treated has been determined to have a hematocrit level of less than about 33% of total blood volume, e.g., is diagnosed as anemic. The VEGF antagonist of the invention is administered in a therapeutically effective amount sufficient to produce an increase in hematocrit above 33% of total blood volume.

In a fourth aspect, the invention features a method of increasing erythropoietin levels in a subject in need thereof, comprising administering to a human subject a vascular endothelial growth factor (VEGF) antagonist comprising a fusion polypeptide having an immunoglobulin-like (Ig) domain 2 of the VEGF receptor Flt1 and Ig domain 3 of the VEGF receptor Flk1 or Flt4, and a multimerizing component.

In a fourth aspect, the invention features a method of stimulating erythropoiesis in a subject in need thereof, comprising administering to a human subject a vascular endothelial growth factor (VEGF) antagonist comprising a fusion polypeptide having an immunoglobulin-like (Ig) domain 2 of the VEGF receptor Flt1 and Ig domain 3 of the VEGF receptor Flk1 or Flt4, and a multimerizing component.

Other objects and advantages will become apparent from a review of the ensuing detailed description.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety.

Definitions

By the term "therapeutically effective dose" is meant a dose that produces the desired effect for which it is administered. The exact dose will depend on the purpose of the treatment, and will be ascertainable by one skilled in the art using known techniques (see, for example, Lloyd (1999) The Art, Science and Technology of Pharmaceutical Compounding).

By the term "blocker", "inhibitor", or "antagonist" is meant a substance that retards or prevents a chemical or physiological reaction or response. Common blockers or inhibitors include but are not limited to antisense molecules, antibodies, antagonists and their derivatives. More specifically, an example of a VEGF antagonist is, for example, an anti-VEGF antibody, or a VEGF-binding receptor-based fusion protein ("trap") such as VEGFR1R2-FcΔC1(a) (SEQ ID NOs:1-2). For a complete description of VEGF-receptor based antagonists including VEGFR1R2-FcΔC1(a), see PCT publication WO/00/75319, the contents of which is incorporated in its entirety herein by reference.

The term "erythropoiesis" denotes the proliferation and/or differentiation of erythroid precursor cells. Standard measures of erythroid cell proliferation and differentiation include hematocrit and reticulocyte counts. Hematocrit is a measurement of red blood cells, and is commonly expressed as the percentage of total blood volume which consists of erythrocytes. Reticulocyte counts measure 1-2 day-old cells that contain mRNA (absent in mature erythrocytes) and aggregates of ribosomes as demonstrated by staining (Erslev, A., "Reticulocyte Enumeration", in Hematology, McGraw-Hill, NY, 1990). A reticulocyte count is the percentage of such cells per 500 or 1000 cells counted. An average range for reticulocyte counts is 0.8% to 1.2%. EPO is commercially available (R & D Systems, Minneapolis, Minn. and Amgen, Thousand Oaks, Calif.) and activity is measured by calibration against the second international reference preparation of erythropoietin (Annable et al. (1972) Bull. Wld. Hlth. Org. 47:99) using an in vivo assay which measures the incorporation of $^{56}$Fe into red blood cells of exhypoxic polycythemic mice (Cotes et al. (1961) Nature 191:1065) or by in vitro cell proliferation assay that uses a factor-dependent human erythroleukemic cell line, TF-1 (Kitamura et al. (1989) J. Cell. Physiol. 140:323). See also, U.S. Pat. No. 6,099,830, herein specifically incorporated by reference in its entirety.

General Description

Anemia is a deficiency in the production of red blood cells (erythrocytes) resulting in a reduction in the level of oxygen transported by blood to the tissues of the body. Hypoxia may be caused by loss of large amounts of blood through hemorrhage, destruction of red blood cells from exposure to autoantibodies, radiation or chemicals, or reduction in oxygen intake due to high altitudes or prolonged unconsciousness. When hypoxia is present in tissue, EPO production is stimulated and increases red blood cell production. EPO promotes the conversion of primitive precursor cells in the bone marrow into pro-erythrocytes which subsequently mature, synthesize hemoglobin and are released into the circulation as red blood cells. When the number of red blood cells in circulation is greater than needed for normal tissue oxygen requirements, the level of EPO in circulation is decreased.

Severe reductions in both megakaryocyte and erythrocyte levels can be associated with the treatment of various cancers with chemotherapy and radiation and diseases such as AIDS, aplastic anemia and myelodysplasias. Levels of megakaryocytes and/or erythrocytes that become too low, for example, platelet counts below 25,000 to 50,000 and hematocrits of less than 25%, are likely to produce considerable morbidity and in certain circumstances these levels are life-threatening. In addition to treating the underlying disease, specific treatments include platelet transfusions for thrombocytopenia (low platelet counts) and stimulation of erythropoiesis using EPO or transfusion of red blood cells for anemia.

As shown in the experimental section below, it is now shown that administration of a VEGF antagonist results in an increased hematocrit. Previous studies (Gerber et al. (1999) Development 126:1149-1159) reported that VEGF blockade in developing mice caused an increase in hematocrit as well as in levels of erythropoietin message in kidney; however, it was suggested that these changes were side effects of cardiac and/or pulmonary hypoplasia. A small molecule inhibitor of the VEGF receptor Flt-1/KDR, SU5416 (semaxanib; Pharmacia), was reported to increase hematocrit in several patients participating in a clinical trial, but this was attributed to the specific cancer they had since it was not observed in other patients (Richard et al. (2002) Blood 99:3851-3853). These results demonstrates that endogenous VEGF is a regulator of erythropoiesis in a broad range of species, including mice, monkeys and humans.

VEGF Antagonists and VEGF-Specific Fusion Polypeptide Traps

The methods of the invention may be achieved with the use of a broad range of VEGF antagonists, including the soluble receptor-based fusion protein described below, an anti-VEGF antibody such as bevacizumab (AVASTIN®; Genentech), and agents capable of blocking VEGF activity for example, CDP-791 (ImClone), sorafenib (NEXAVAR®, Bayer AG), sunitnib (SUTENT®, Pfizer).

In a preferred embodiment, the VEGF antagonist is a dimeric protein capable of binding VEGF with a high affinity composed of two receptor-Fc fusion protein consisting of the principal ligand-binding portions of the human VEGFR1 and VEGFR2 receptor extracellular domains fused to the Fc portion of human IgG1. Specifically, the VEGF trap consists of Ig domain 2 from VEGFR1, which is fused to Ig domain 3 from VEGFR2, which in turn is fused to the Fc domain of IgG1 (SEQ ID NO:2).

The nucleic acid constructs encoding the fusion proteins useful in the methods of the invention are inserted into an expression vector by methods known to the art, wherein the nucleic acid molecule is operatively linked to an expression control sequence. Host-vector systems for the production of proteins comprising an expression vector introduced into a host cell suitable for expression of the protein are known in the art. The suitable host cell may be a bacterial cell such as *E. coli*, a yeast cell, such as *Pichia pastoris*, an insect cell, such as *Spodoptera frugiperda*, or a mammalian cell, such as a COS, CHO, 293, BHK or NS0 cell. In a preferred embodiment, an expression plasmid encoding the VEGF trap is transfected into CHO cells, which secrete VEGF trap into the culture medium. The resulting VEGF trap is a dimeric glycoprotein with a protein molecular weight of 97 kDa and contains ~15% glycosylation to give a total molecular weight of 115 kDa.

Since the VEGF trap binds its ligands using the binding domains of high-affinity receptors, it has a greater affinity for VEGF than do monoclonal antibodies. The VEGF trap binds VEGF-A with a $K_D$ of approximately about 1.5 pM, PLGF1 with a $K_D$ of approximately about 1.3 nM, and PLGF2 with a $K_D$ of approximately about 50 pM; binding to other VEGF family members has not yet been fully characterized.

Treatment Population

Subjects undergoing cancer treatment with chemotherapeutic agents and/or radiation are known to suffer severe reduction win megakaryocyte and/or erythrocyte levels and become anemic. Subjects suffering from diseases such as AIDS, aplastic anemia and myelodysplasias are similarly known to become anemic. Generally, a subject is considered anemic if their hemoglobin levels fall below 11-13 gm/100 ml of blood (depending upon the age and sex of the patient Accordingly, a subject at risk for development of anemia or suffering from anemia is a candidate for treatment by the methods of the invention.

Combination Therapies

In numerous embodiments, a VEGF antagonist may be administered in combination with one or more additional compounds or therapies, including a second VEGF antagonist molecule. Combination therapy includes administration of a single pharmaceutical dosage formulation which contains a VEGF antagonist and one or more additional agents; as well as administration of a VEGF antagonist and one or more additional agent(s) in its own separate pharmaceutical dosage formulation. For example, a VEGF antagonist and a cytotoxic agent, a chemotherapeutic agent or a growth inhibitory agent can be administered to the patient together in a single dosage composition such as a combined formulation, or each agent can be administered in a separate dosage formulation. Where separate dosage formulations are used, the VEGF-specific fusion protein of the invention and one or more additional agents can be administered concurrently, or at separately staggered times, i.e., sequentially.

The term "cytotoxic agent" as used herein refers to a substance that inhibits or prevents the function of cells and/or causes destruction of cells. The term is intended to include radioactive isotopes (e.g. $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include alkylating agents such as thiotepa and cyclophosphamide (Cytoxan®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (Taxol®, Bristol-Myers Squibb Oncology, Princeton, N.J.) and docetaxel (Taxotere®; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

A "growth inhibitory agent" when used herein refers to a compound or composition which inhibits growth of a cell, especially a cancer cell either in vitro or in vivo. Examples of growth inhibitory agents include agents that block cell cycle progression (at a place other than S phase), such as agents that induce G1 arrest and M-phase arrest. Classical M-phase blockers include the vincas (vincristine and vinblastine), Taxol®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C.

Methods of Administration

The invention provides compositions and methods of treatment comprising a VEGF antagonist, such as a VEGF antagonist, and an anti-hypertensive agent. Various delivery systems are known and can be used to administer the composition of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intraperitoneal, intravenous, subcutaneous, intranasal, intraocular, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Administration can be acute or chronic (e.g. daily, weekly, monthly, etc.) or in combination with other agents. Pulmonary administration can also be employed, e.g., by use of an inhaler or nebulizer, and formulation with an aerosolizing agent.

In another embodiment, the active agent can be delivered in a vesicle, in particular a liposome, in a controlled release system, or in a pump. In another embodiment where the active agent of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), by direct injection, or by use of microparticle bombardment, or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, the implant being of a porous, non-porous, or gelatinous material, including membranes, such as silastic membranes, fibers, or commercial skin substitutes.

A composition useful in practicing the methods of the invention may be a liquid comprising an agent of the invention in solution, in suspension, or both. The term "solution/suspension" refers to a liquid composition where a first portion of the active agent is present in solution and a second portion of the active agent is present in particulate form, in suspension in a liquid matrix. A liquid composition also includes a gel. The liquid composition may be aqueous or in the form of an ointment.

An aqueous suspension or solution/suspension useful for practicing the methods of the invention may contain one or more polymers as suspending agents. Useful polymers include water-soluble polymers such as cellulosic polymers and water-insoluble polymers such as cross-linked carboxyl-containing polymers. An aqueous suspension or solution/suspension of the present invention is preferably viscous or muco-adhesive, or even more preferably, both viscous and mucoadhesive.

Pharmaceutical Compositions

Pharmaceutical compositions useful in the practice of the method of the invention include a therapeutically effective amount of an active agent, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

In a preferred embodiment, the composition is formulated in accordance with routine procedures as a pharmaceutical composition adapted for intravenous, subcutaneous, or intramuscular administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The active agents of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the active agent of the invention that will be effective in the treatment of diabetes can be determined by standard clinical techniques based on the present description. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. However, suitable dosage ranges for intravenous administration are generally about 50-5000 micrograms of active compound per kilogram body weight. Suitable dosage ranges for intranasal administration are generally about 0.01 pg/kg body weight to 10 mg/kg body weight. Effective doses may be extrapolated from dose-response curves derived from in vitro or animal model test systems.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds that are sufficient to maintain therapeutic effect. One having skill in the art will be able to optimize therapeutically effective local dosages without undue experimentation.

The amount of compound administered will, of course, be dependent on the subject being treated, on the subject's weight, the severity of the affliction, the manner of administration, and the judgment of the prescribing physician. The therapy may be repeated intermittently while symptoms are detectable or even when they are not detectable. The therapy may be provided alone or in combination with other drugs.

Other features of the invention will become apparent in the course of the following descriptions of exemplary embodiments which are given for illustration of the invention and are not intended to be limiting thereof.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Effect of VEGF Trap Administration on Hematocrit in Mice

Figure 1:
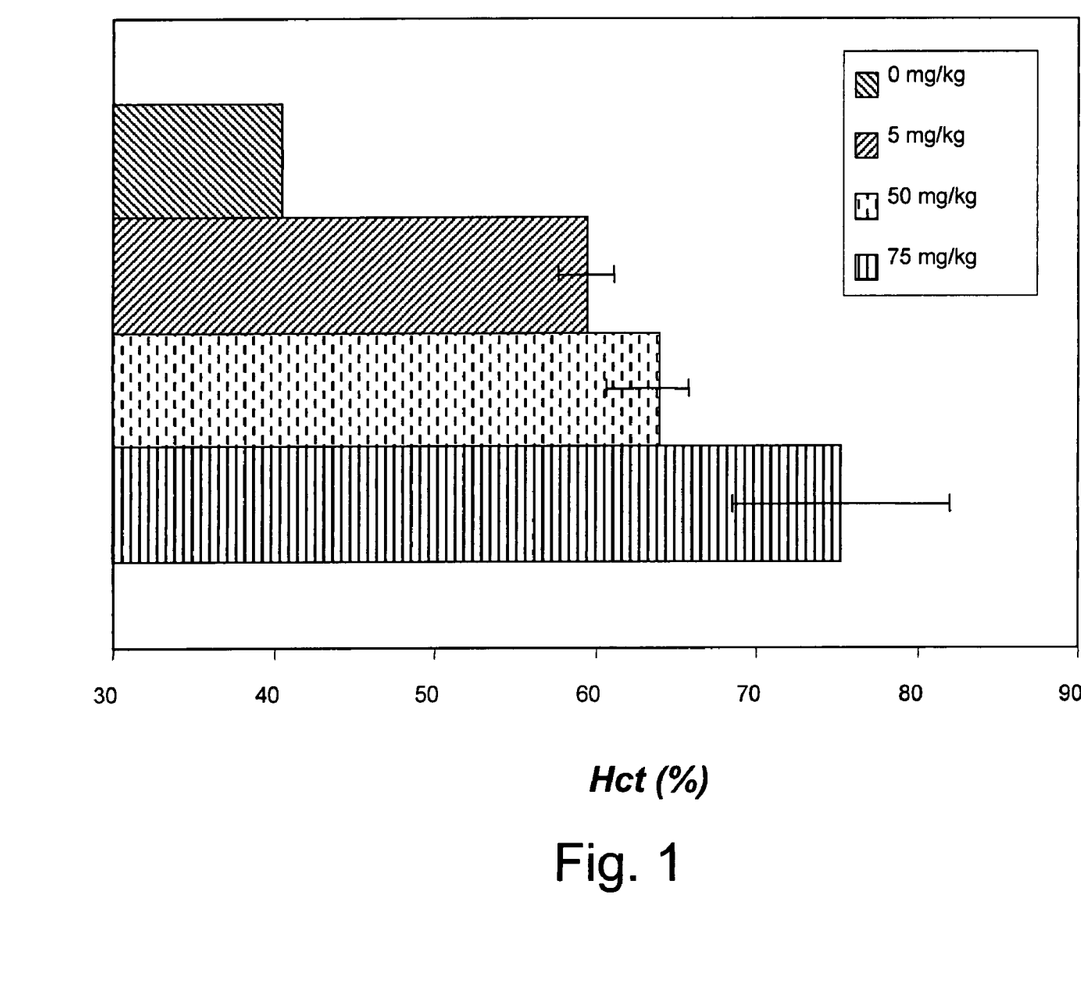
FIG. 1 is a bar graph of percent hematocrit increase in SCID mice (n=3-4 per group) treated with cumulative weekly doses of 5, 50, or 75 mg/kg VEGF trap protein (SEQ ID NO:4) delivered by subcutaneous injection. Hematocrit was measured at 8 and 9.5 weeks, Control hematocrit data (0 ug/kg) is based on data obtained from mice sacrificed at 8 weeks.

SCID mice (n=3-4) were treated with VEGF trap protein (SEQ ID NO:4) injected subcutaneously twice weekly (cumulative weekly doses of 5 and 50 mg/kg) or thrice iweekly (cumulative weekly dose of 75 mg/kg) over a period of 8 or 9.5 weeks, respectively. Hematocrit was measured by standard technique. The results are shown in FIG. 1. Increased hematocrit was observed in a dose-dependant manner in SCID mice treated with VEGF trap.

Figure 2:
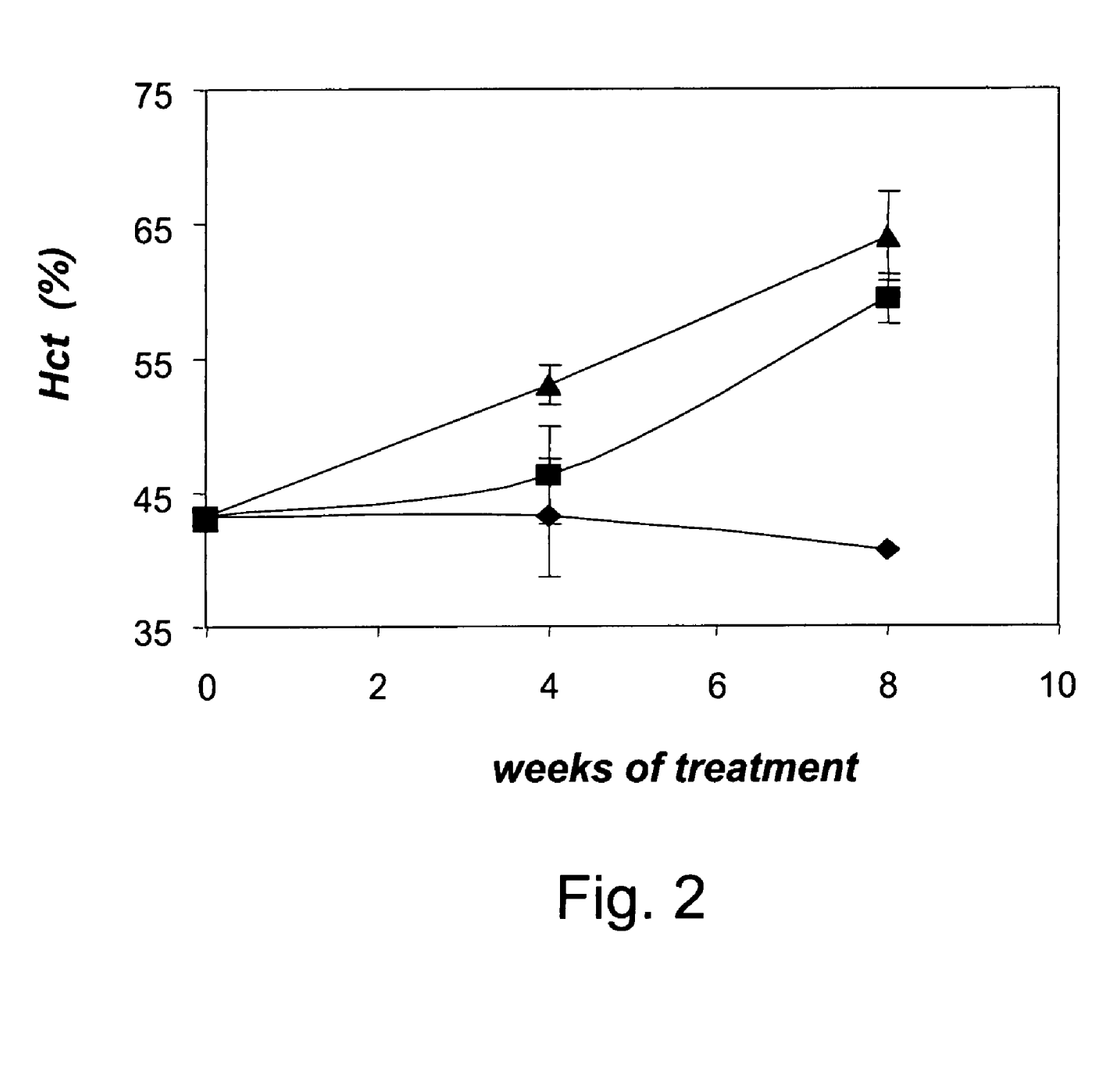
FIG. 2 is a graph showing the effect of varying amounts of VEGF trap administered over an 8 week period by subcutaneous twice weekly injection to mice with the indicated doses being the cumulative weekly dose (♦=0 mg/kg; ■=5 mg/kg; ▲=50 mg/kg). Hematocrit at day 0 is based on historical hematocrit data from mice of the same strain and approximate age.

Mice were treated with twice weekly subcutaneous injections of 2.5 or 25 mg/kg for 4 or 8 week periods. Hematocrit levels were measured in mice sacrificed 4 and 8 weeks. The results are shown in FIG. 2. Increased hematocrit was observed in mice in both VEGF trap dosing cohorts after 4 weeks of treatment and this effect became more pronounced with extended treatment Example 2

Effect of VEGF Trap Administration on Hematocrit in Monkeys

Twenty-four cynomolgus monkeys (3/sex/group) were administered subcutaneously 1.5, 5 or 15 mg/kg VEGF trap protein (SEQ ID NO;4) or vehicle three times a week for four weeks. Eight additional cynomolgus monkeys (2/sex/group) received either vehicle or 15 mg/kg VEGF trap protein three times a week for four weeks with an additional 28-day recovery period. An increase in hematocrit, hemoglobin and red blood cell counts was observed at all doses.

Figure 3:
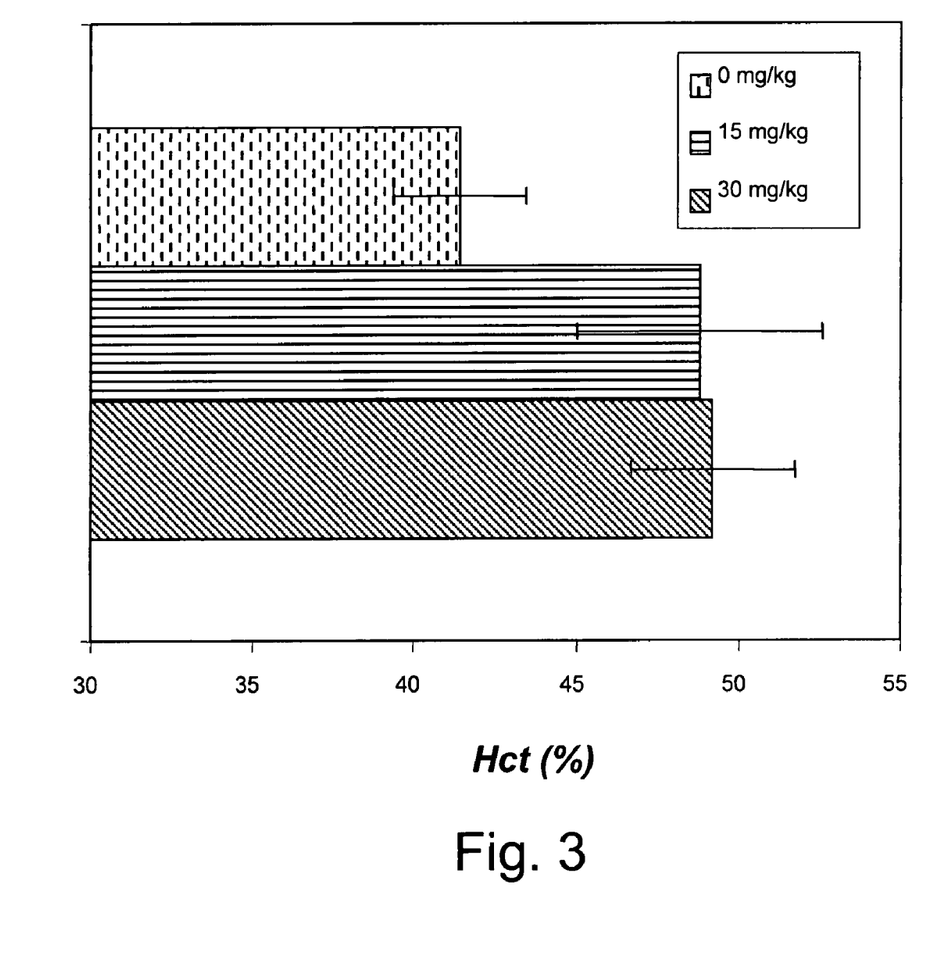
FIG. 3 is a bar graph of changes in hematocrit observed at 13 weeks in monkeys (n=6) treated biweekly with 0 (control), 15 or 30 mg/kg of VEGF trap protein.

Cynomolgus monkeys (n=6) were subcutaneously injected biweekly with VEGF trap protein (SEQ ID NO:4) at 15 and 30 mg/kg. Hematocrit levels were determined at 13 weeks of treatment. Results are shown in FIG. 3.

Example 3

Effect of VEGF Trap Administration on Hematocrit in Mice

VEGF Trap was administered twice weekly via subcutaneous injection at doses ranging between 0 and 25 mg/kg for periods ranging from 10 days to 8 weeks. At the termination of the study, whole blood was obtained by cardiac puncture and sent to AniLytics (Gaithersburg, Md.) for analysis including determination of hematocrit. "IgG4" refers to a version of the VEGF trap protein in which IgG4 is substituted for IgG1; "cremophor" is a vehicle for paclitaxel (Taxol™) comprising 10% cremophor, 10% ethanol in PBS; Taxol™ was given as 20 mg/kg three times per week. When mice are treated with VEGF Trap, hematocrit is increased regardless of the strain of mouse. In general, effects of VEGF trap treatment on hematocrit appear to be dependant on both duration of treatment as well as dose. When VEGF trap was combined with an agent that alone resulted in decreased hematocrit, hematocrit was found to be at approximately normal levels.

TABLE 1

Effect of VEGF Trap Administration on Hematocrit

| Experiment | Strain/sex | Duration | Dose VEGF Trap | % Hematocrit |
|---|---|---|---|---|
| VGT1 | CD-1/F | 10 days | 0 | 42.7 ± 1.4 |
| | | | 2.5 mg/kg | 35.3 ± 3.7 |
| | | | 25 mg/kg | 37.8 |
| | CD-1/M | 10 days | 0 | 38.4 ± 3.2 |
| | | | 2.5 mg/kg | 39.5 ± 3.6 |
| | | | 25 mg/kg | 48.3 ± 3.6 |
| VGT2 | SCID/F | 3 weeks | 0 | 40.1 ± 1.3 |
| | | | 25 mg/kg | 49 ± 2.9 |
| | SCID/M | 3 weeks | 0 | 39.5 ± 2.8 |
| | | | 25 mg/kg | 56.0 ± 0.6 |
| VGT3 | SCID/M (15 weeks) | 4 weeks | 0 | 38.3 ± 0.6 |
| | | | 2.5 mg/kg | 42.8 ± 4.1 |
| | | | 25 mg/kg | 48.2 ± 4.8 |
| | SCID/M (7 weeks) | 4 weeks | 0 | 43.1 ± 0.6 |
| | | | 2.5 mg/kg | 46.3 ± 3.7 |
| | | | 25 mg/kg | 53.0 ± 1.5 |
| | SCID/M (15 weeks) | 8 weeks | 0 | 39 |
| | | | 2.5 mg/kg | 57.7 ± 1.8 |
| | | | 25 mg/kg | 62.2 ± 3.3 |
| | SCID/M (7 weeks) | 8 weeks | 0 | 40.6 ± 1.1 |
| | | | 2.5 mg/kg | 59.4 ± 2.0 |
| | | | 25 mg/kg | 64.0 ± 3.2 |
| VGT4 | SCID/M | 8 weeks | 0 | 40.5 ± 1.6 |
| | | | 5 mg/kg | 55.2 ± 1.7 |
| | | | 5 mg/kg IgG4 | 53.8 ± 1.7 |
| VGT5 | Nod/SCID/M | 4 weeks | 0 | 33.7 ± 2.5 |
| | | | 2.5 mg/kg | 37.4 ± 6.8 |
| | | | 25 mg/kg | 41.6 ± 1.1 |
| | | 6 weeks | 0 | 35.3 ± 0.7 |
| | | | 2.5 mg/kg | 41.1 ± 2.3 |
| | | | 25 mg/kg | 46.0 ± 4.7 |
| VGT6 | SCID | 8 weeks | 0 | 41.4 ± 3.4 |
| | | | 5 mg/kg | 58.4 ± 3.2 |
| | | | 25 mg/kg | 54.1 ± 0.6 |
| VGT8 | SCID | 4 weeks | 0 | 40.9 ± 2.3 |
| | | | 25 mg/kg | 51.4 ± 0.6 |
| | C57B1/6 | 4 weeks | 0 | 43.2 ± 0.8 |
| | | | 25 mg/kg | 59.5 ± 1.4 |
| VTC1 | Nude | 4 weeks | Taxol ™ | 36.2 ± 0 |
| | | | Cremophor | 41.5 ± 1.7 |
| | | | 0 | 42.4 ± 0.4 |
| | | | 1 mg/kg + Taxol ™ | 42.3 ± 1.3 |
| | | | 5 mg/kg + Taxol ™ | 51.2 |
| | | | 25 mg/kg + Taxol ™ | 45.6 |
| | | | 25 mg/kg + cremophor ™ | 46.1 ± 6.7 |
| | | | 25 mg/kg | 49.5 ± 1.8 |

Example 4

Effect of VEGF Trap on Hematocrit in Human Patients

A clinical trial was conducted with VEGF trap protein (SEQ ID NO:4) administered subcutaneously into subjects with incurable relapased or refractory solid tumors, other than squamous-cell lung cancer. Subjects were treated with VEGF trap protein at 25, 50, 100, 200, 400, and 800 μg/kg weekly, and 800 μg/kg twice weekly. Beginning in the fifth week of study, subjects received a series of 6 weekly (or twice weekly) injections at the assigned dose level.

A dose-related increase in hematocrit values was observed between baseline and visit 16. Hematocrit values changed by +3.8%, +2.7%, −0.2%, +1.6%, +0.6% and +0.1% in the 800 μg/kg twice weekly and weekly groups, and 400, 200, 100, 50, and 25 μg/kg dose level cohorts, respectively. Similar observations were seen for hemoglobin.

Dose level cohorts were combined into 4 dose groups to facilitate the use statistical tools to examine the trends in hemoglobin and hematocrit by creating groups for analysis with approximately equal numbers of subjects. Combined dose group 1 included subjects treated at the 25, 50, and 100 μg/kg (combined n=13); combined dose group 2 included subjects treated at the 200 and 400 μg/kg dose levels (combined n=10); combined dose group 3 included subjects treated at the 800 μg/kg once weekly dose level (n-7), and dose group 4 included subjects treated at the 800 μg/kg twice weekly dose level (n=8). While mean hematocrit did not increase in the cohort of patients in the lowest dose group (25, 50 and 100 mg), in each of the other three groups an increase in hematocrit was apparent after 4 weeks of treatment. After 10 weeks of treatment this effect was most pronounced in the two highest dose groups (800 mg once or twice weekly).

We claim:

1. A method of treating an anemic disorder in a human subject in need thereof, comprising administering to the human subject a vascular endothelial growth factor (VEGF) antagonist capable of blocking, inhibiting, or ameliorating VEGF-mediated activity, wherein the VEGF antagonist is fusion polypeptide VEGRF1R2-FcΔC1(a) (SEQ ID NO:4).

2. The method of claim 1, wherein the anemic disorder is characterized by a reduced hematocrit level.

3. The method of claim 1, wherein the anemic disorder is associated with chronic renal failure, cancer, cancer chemotherapy, radiation treatment, antiviral therapy, nutritional iron-deficiency, blood-loss, or hemolysis.

4. The method of claim 3, wherein the anemic disorder results from treatment with chemotherapy or radiation.

5. The method of claim 1, wherein administration is subcutaneous or intravenous.

6. The method of claim 5 wherein administration is a single dose or multiple doses.

7. A method of treating anemia expected to result from cancer treatment in a human subject at risk, comprising administering to the human subject fusion polypeptide VEGRF1R2-FcΔC1(a) (SEQ ID NO:4).

8. The method of claim 7, wherein cancer treatment is treatment with radiation and/or chemotherapy.

9. A method of increasing hematocrit level in a human subject in need thereof, comprising administering to the human subject a vascular endothelial growth factor (VEGF) antagonist comprising fusion polypeptide VEGRF1R2-FcΔC1(a) (SEQ ID NO:4).

10. The method of claim 9, wherein the hematocrit level in a subject in need thereof is less than about 33% of total blood volume and administration of the fusion polypeptide is in an amount sufficient to increase the hematocrit level above 33% of total blood volume.

11. A method of increasing erythropoietin levels in a human subject in need thereof, comprising administering to the human subject a vascular endothelial growth factor (VEGF) antagonist comprising fusion polypeptide VEGRF1R2-FcΔC1(a) (SEQ ID NO:4).

12. A method of stimulating erythropoiesis in a human subject in need thereof, comprising administering to the human subject a vascular endothelial growth factor (VEGF) antagonist comprising fusion polypeptide VEGRF1R2-FcΔC1(a) (SEQ ID NO:4).

* * * * *

SEQUENCE LISTING

<160> NUMBER OF SEQ ID NOS: 4

<210> SEQ ID NO 1
<211> LENGTH: 1453
<212> TYPE: DNA
<213> ORGANISM: Artificial Sequence
<220> FEATURE:
<223> OTHER INFORMATION: Synthetic

<400> SEQUENCE: 1

| | | | | | |
|---|---|---|---|---|---|
| aagcttgggc | tgcaggtcga | tcgactctag | aggatcgatc | cccgggcgag | ctcgaattcg | 60 |
| caaccaccat | ggtcagctac | tgggacaccg | ggtcctgct | gtgcgcgctg | ctcagctgtc | 120 |
| tgcttctcac | aggatctagt | tccgaggta | gacctttcgt | agagatgtac | agtgaaatcc | 180 |
| ccgaaattat | acacatgact | gaaggaaggg | agctcgtcat | tccctgccgg | gttacgtcac | 240 |
| ctaacatcac | tgttacttta | aaaaagtttc | cacttgacac | tttgatccct | gatggaaaac | 300 |
| gcataatctg | ggacagtaga | aagggcttca | tcatatcaaa | tgcaacgtac | aaagaaatag | 360 |
| ggcttctgac | ctgtgaagca | acagtcaatg | ggcatttgta | taagacaaac | tatctcacac | 420 |
| atcgacaaac | caatacaatc | atagatgtgg | ttctgagtcc | gtctcatgga | attgaactat | 480 |
| ctgttggaga | aaagcttgtc | ttaaattgta | cagcaagaac | tgaactaaat | gtggggattg | 540 |
| acttcaactg | gaatacccct | tcttcgaagc | atcagcataa | gaaacttgta | aaccgagacc | 600 |
| taaaaaccca | gtctgggagt | gagatgaaga | aatttttgag | caccttaact | atagatggtg | 660 |
| taacccggag | tgaccaagga | ttgtacacct | gtgcagcatc | cagtgggctg | atgaccaaga | 720 |
| agaacagcac | atttgtcagg | gtccatgaaa | agggcccggg | cgacaaaact | cacacatgcc | 780 |
| caccgtgccc | agcacctgaa | ctcctggggg | gaccgtcagt | cttcctcttc | cccccaaaac | 840 |
| ccaaggacac | cctcatgatc | tcccggaccc | ctgaggtcac | atgcgtggtg | gtggacgtga | 900 |
| gccacgaaga | ccctgaggtc | aagttcaact | ggtacgtgga | cggcgtggag | gtgcataatg | 960 |
| ccaagacaaa | gccgcgggag | gagcagtaca | acagcacgta | ccgtgtggtc | agcgtcctca | 1020 |
| ccgtcctgca | ccaggactgg | ctgaatggca | aggagtacaa | gtgcaaggtc | tccaacaaag | 1080 |
| ccctcccagc | ccccatcgag | aaaaccatct | ccaaagccaa | agggcagccc | cgagaaccac | 1140 |
| aggtgtacac | cctgccccca | tcccgggatg | agctgaccaa | gaaccaggtc | agcctgacct | 1200 |
| gcctggtcaa | aggcttctat | cccagcgaca | tcgccgtgga | gtgggagagc | aatgggcagc | 1260 |
| cggagaacaa | ctacaagacc | acgcctcccg | tgctggactc | cgacggctcc | ttcttcctct | 1320 |
| atagcaagct | caccgtggac | aagagcaggt | ggcagcaggg | gaacgtcttc | tcatgctccg | 1380 |
| tgatgcatga | ggctctgcac | aaccactaca | cgcagaagag | cctctccctg | tctccgggta | 1440 |
| aatgagcggc | cgc | | | | | 1453 |

<210> SEQ ID NO 2
<211> LENGTH: 458
<212> TYPE: PRT
<213> ORGANISM: Artificial Sequence
<220> FEATURE:
<223> OTHER INFORMATION: Synthetic

<400> SEQUENCE: 2

Met Val Ser Tyr Trp Asp Thr Gly Val Leu Leu Cys Ala Leu Leu Ser
1               5                   10                  15

Cys Leu Leu Leu Thr Gly Ser Ser Ser Gly Gly Arg Pro Phe Val Glu
            20                  25                  30

```
Met Tyr Ser Glu Ile Pro Glu Ile Ile His Met Thr Glu Gly Arg Glu
         35                  40                  45

Leu Val Ile Pro Cys Arg Val Thr Ser Pro Asn Ile Thr Val Thr Leu
         50                  55                  60

Lys Lys Phe Pro Leu Asp Thr Leu Ile Pro Asp Gly Lys Arg Ile Ile
 65                  70                  75                  80

Trp Asp Ser Arg Lys Gly Phe Ile Ile Ser Asn Ala Thr Tyr Lys Glu
                 85                  90                  95

Ile Gly Leu Leu Thr Cys Glu Ala Thr Val Asn Gly His Leu Tyr Lys
                100                 105                 110

Thr Asn Tyr Leu Thr His Arg Gln Thr Asn Thr Ile Ile Asp Val Val
            115                 120                 125

Leu Ser Pro Ser His Gly Ile Glu Leu Ser Val Gly Glu Lys Leu Val
        130                 135                 140

Leu Asn Cys Thr Ala Arg Thr Glu Leu Asn Val Gly Ile Asp Phe Asn
145                 150                 155                 160

Trp Glu Tyr Pro Ser Ser Lys His Gln His Lys Lys Leu Val Asn Arg
                165                 170                 175

Asp Leu Lys Thr Gln Ser Gly Ser Glu Met Lys Lys Phe Leu Ser Thr
            180                 185                 190

Leu Thr Ile Asp Gly Val Thr Arg Ser Asp Gln Gly Leu Tyr Thr Cys
        195                 200                 205

Ala Ala Ser Ser Gly Leu Met Thr Lys Lys Asn Ser Thr Phe Val Arg
    210                 215                 220

Val His Glu Lys Gly Pro Gly Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445
```

-continued

Gln Lys Ser Leu Ser Leu Ser Pro Gly Lys
    450                 455

<210> SEQ ID NO 3
<211> LENGTH: 1377
<212> TYPE: DNA
<213> ORGANISM: Artificial Sequence
<220> FEATURE:
<223> OTHER INFORMATION: Synthetic

<400> SEQUENCE: 3

```
atggtcagct actgggacac cggggtcctg ctgtgcgcgc tgctcagctg tctgcttctc      60
acaggatcta gttccggaag tgataccggt agacctttcg tagagatgta cagtgaaatc     120
cccgaaatta tacacatgac tgaaggaagg gagctcgtca ttccctgccg ggttacgtca     180
cctaacatca ctgttacttt aaaaaagttt ccacttgaca ctttgatccc tgatggaaaa     240
cgcataatct gggacagtag aaagggcttc atcatatcaa atgcaacgta caaagaaata     300
gggcttctga cctgtgaagc aacagtcaat gggcatttgt ataagacaaa ctatctcaca     360
catcgacaaa ccaatacaat catagatgtg gttctgagtc cgtctcatgg aattgaacta     420
tctgttggag aaaagcttgt cttaaattgt acagcaagaa ctgaactaaa tgtggggatt     480
gacttcaact gggaataccc ttcttcgaag catcagcata gaaacttgt aaaccgagac     540
ctaaaaaccc agtctgggag tgagatgaag aaattttga gcaccttaac tatagatggt     600
gtaacccgga gtgaccaagg attgtacacc tgtgcagcat ccagtgggct gatgaccaag     660
aagaacagca catttgtcag ggtccatgaa aaggacaaaa ctcacacatg cccaccgtgc     720
ccagcacctg aactcctggg gggaccgtca gtcttcctct tccccccaaa acccaaggac     780
accctcatga tctcccggac ccctgaggtc acatgcgtgg tggtggacgt gagccacgaa     840
gaccctgagg tcaagttcaa ctggtacgtg gacggcgtgg aggtgcataa tgccaagaca     900
aagccgcggg aggagcagta caacagcacg taccgtgtgg tcagcgtcct caccgtcctg     960
caccaggact ggctgaatgg caaggagtac aagtgcaagg tctccaacaa agccctccca    1020
gcccccatcg agaaaaccat ctccaaagcc aagggcagc cccgagaacc acaggtgtac    1080
accctgcccc catcccggga tgagctgacc aagaaccagg tcagcctgac ctgcctggtc    1140
aaaggcttct atcccagcga catcgccgtg gagtgggaga gcaatgggca gccggagaac    1200
aactacaaga ccacgcctcc cgtgctggac tccgacggct ccttcttcct ctacagcaag    1260
ctcaccgtgg acaagagcag gtggcagcag gggaacgtct tctcatgctc cgtgatgcat    1320
gaggctctgc acaaccacta cacgcagaag agcctctccc tgtctccggg taaatga      1377
```

<210> SEQ ID NO 4
<211> LENGTH: 458
<212> TYPE: PRT
<213> ORGANISM: Artificial Sequence
<220> FEATURE:
<223> OTHER INFORMATION: Synthetic

<400> SEQUENCE: 4

Met Val Ser Tyr Trp Asp Thr Gly Val Leu Leu Cys Ala Leu Leu Ser
 1               5                  10                  15

Cys Leu Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr

```
                50                  55                  60
Val Thr Leu Lys Lys Phe Pro Leu Asp Thr Leu Ile Pro Asp Gly Lys
 65                  70                  75                  80

Arg Ile Ile Trp Asp Ser Arg Lys Gly Phe Ile Ile Ser Asn Ala Thr
                     85                  90                  95

Tyr Lys Glu Ile Gly Leu Leu Thr Cys Glu Ala Thr Val Asn Gly His
                    100                 105                 110

Leu Tyr Lys Thr Asn Tyr Leu Thr His Arg Gln Thr Asn Thr Ile Ile
                    115                 120                 125

Asp Val Val Leu Ser Pro Ser His Gly Ile Glu Leu Ser Val Gly Glu
130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                    165                 170                 175

Val Asn Arg Asp Leu Lys Thr Gln Ser Gly Ser Glu Met Lys Lys Phe
                    180                 185                 190

Leu Ser Thr Leu Thr Ile Asp Gly Val Thr Arg Ser Asp Gln Gly Leu
                    195                 200                 205

Tyr Thr Cys Ala Ala Ser Ser Gly Leu Met Thr Lys Lys Asn Ser Thr
                    210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
                    245                 250                 255

Lys Pro Lys Asp Thr Leu Met Ile Ser Arg Thr Pro Glu Val Thr Cys
                    260                 265                 270

Val Val Val Asp Val Ser His Glu Asp Pro Glu Val Lys Phe Asn Trp
                    275                 280                 285

Tyr Val Asp Gly Val Glu Val His Asn Ala Lys Thr Lys Pro Arg Glu
                    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                    325                 330                 335

Lys Ala Leu Pro Ala Pro Ile Glu Lys Thr Ile Ser Lys Ala Lys Gly
                    340                 345                 350

Gln Pro Arg Glu Pro Gln Val Tyr Thr Leu Pro Pro Ser Arg Asp Glu
                    355                 360                 365

Leu Thr Lys Asn Gln Val Ser Leu Thr Cys Leu Val Lys Gly Phe Tyr
                    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                    405                 410                 415

Leu Tyr Ser Lys Leu Thr Val Asp Lys Ser Arg Trp Gln Gln Gly Asn
                    420                 425                 430

Val Phe Ser Cys Ser Val Met His Glu Ala Leu His Asn His Tyr Thr
                    435                 440                 445

Gln Lys Ser Leu Ser Leu Ser Pro Gly Lys
                    450                 455
```